US005692055A

United States Patent [19]

Sano et al.

[11] Patent Number: 5,692,055

[45] Date of Patent: Nov. 25, 1997

[54] ACTIVE NOISE-SUPPRESSIVE CONTROL METHOD AND APPARATUS

[75] Inventors: Hisashi Sano, Wako; Shuichi Adachi, Utsunomiya, both of Japan

[73] Assignee: Honda Giken Kogyo Kabushiki Kaisha, Tokyo, Japan

[21] Appl. No.: 719,027

[22] Filed: Sep. 24, 1996

[51] Int. Cl.$^{6}$ .............................. A61F 11/06; H03B 29/00

[52] U.S. Cl. .............................. 381/71; 381/94

[58] Field of Search .............................. 381/71, 94, 86, 381/73.1

[56] References Cited

U.S. PATENT DOCUMENTS

| | | | |
|---|---|---|---|
| 5,337,366 | 8/1994 | Eguchi | 381/94 |
| 5,481,615 | 1/1996 | Eatwell | 381/71 |
| 5,524,057 | 6/1996 | Akiho | 381/71 |

FOREIGN PATENT DOCUMENTS

| | | | |
|---|---|---|---|
| 0539940 | 5/1993 | European Pat. Off. | 381/71 |
| 1-501344 | 5/1989 | Japan . | |
| 6138885 | 5/1994 | Japan | 381/71 |
| 6161473 | 6/1994 | Japan | 381/71 |
| 8-30278 | 2/1996 | Japan . | |
| 8802912 | 4/1988 | WIPO . | |
| 9429848 | 12/1994 | WIPO | 381/71 |

OTHER PUBLICATIONS

*Reports of the 1995 Autumn Meeting of Acoustical Society of Japan*, Sep. 27, 1995.

*Active Adaptive Feedback Control of Sound Field*, Mitsubishi Heavy Industries, Ltd., 1st International conf. on Motion and Vibration Control, Yokohama, Sep. 1992, pp. 1032–1037.

*2–Degree–of Freedom Control Approach to Active Noise Control*, Inter–Noise 94, Toyota Central R & D Labs., Toyota Motor Corporation, Aug. 1994, pp. 1255–1228.

*Feedfoward and Feedback Methods for Active Control*, Proceedings of the Institute of Acoustics; Proc. I.O.A. vol. 16 Part 2, 1994, pp. 255–276.

*Design of Feedback Controllers Using a Feedforward Approach*, Active 95, Jul. 1995, pp. 863–874.

*SISO IMC Design for Stable Systems*, Robust Process Control, M. Morari E. Zafiriou Prentice–Hall 1989, pp. 57–84.

*Primary Examiner*—Minsun Oh

*Attorney, Agent, or Firm*—Birch, Stewart, Kolasch & Birch, LLP

[57] ABSTRACT

A reproduced sound is sent from a speaker as a sound source unit provided in a sound field. An error signal is produced by a microphone on the basis of a difference in sound between the reproduced sound from the speaker and noise coming from the outside of the sound field into the sound field. A digital filter has a fixed transfer function approximated to a transfer function of the sound field, to which a signal for driving the speaker is supplied. Variation of the transfer function of the sound field is detected by the digital filter. A difference signal between the error signal and an output signal from the digital filter is calculated by an adder. The difference signal determined by the adder is inputted into an IMC filter. A signal for compensating the variation of the transfer function of the sound field and variation of the noise is produced by the IMC filter. A variable parameter of the IMC filter is set so that an absolute value of a product of a value of an approximated and set amount of variation, a distance from the sound source unit to the error-detecting unit, and the variable parameter of the IMC filter is less than 1. Thus, the noise coming into the inside of the sound field is canceled by using an output sound of the speaker.

14 Claims, 9 Drawing Sheets

ACTIVE NOISE-SUPPRESSIVE CONTROL METHOD AND APPARATUS

BACKGROUND OF THE INVENTION

1. Field of the Invention

The present invention relates to an active noise-suppressive control method and an apparatus usable to suppress, for example, noise in a vehicle's cabin caused by road noise or the like by producing vibration (including sound) having polarity approximately opposite to polarity of the noise and having an amplitude approximately the same as an amplitude of the noise. In particular, the present invention relates to an active noise-suppressive control method and an apparatus based on an internal model controller system.

2. Description of the Related Art

Conventional active noise-suppressive control is based on feedback control as shown in FIGS. 7A, 7(B) and 8 to 10. Specifically, as shown in FIG. 7(A), this conventional system is constructed as follows. Namely, a microphone 21, which serves as a sensor for error detection, is provided within a noise-suppressive region. A speaker 22, which serves as a sound source for canceling noise by using its output sound, is provided at a position spaced apart from the microphone 21 by a predetermined distance. A difference between the noise and the output sound from the speaker 22 is detected by the microphone 21. An output signal of the microphone 21 is supplied to a feedback controller 23 provided with an adaptive filter. The speaker 22 is driven in accordance with an output of the feedback controller 23 so that the noise is counteracted.

In FIG. 7(A), it is assumed that a transfer function from the speaker 22 to the microphone 21 is represented by P(s), and a transfer function of the feedback controller 23 is represented by K(s). Thus the active noise-suppressive control apparatus shown in FIG. 7(A) is expressed by a block diagram shown in FIG. 7(B). Now a region ranging from the speaker 22 to the microphone 21 is regarded as a plant 24. S represents a complex parameter.

Specifically, the active noise-suppressive control shown in FIG. 7(A) is performed on the basis of adaptive control. Exemplary systems of such control are shown in FIGS. 8, 9, and 10. An exemplary conventional system is schematically shown in a block diagram in FIG. 8, in which a signal obtained by applying howling cancel to an error signal is used as a reference signal to perform feedback type LMS (Least Mean Square) adaptive control. An output signal from a microphone 21 is amplified by an amplifier 21*a*. An amplified output signal of the microphone is converted into a digital signal by an A/D converter 21*b*. A speaker-driving signal having passed through a howling cancel filter 25 described later on is added by an adder 21*c* to an output signal from the A/D converter to obtain a signal as a reference signal in which its howling characteristic is compensated. The reference signal and the output signal from the A/D converter 21*b* are used as inputs to be supplied to an adaptive filter 26 based on feedback type filtered-X-LMS signal processing. An output of the adaptive filter 26 is fed to the howling cancel filter 25. The output of the adaptive filter 26 is also supplied to a D/A converter 22*a* to be converted into an analog signal followed by amplification by an amplifier 22*b*. An output of the amplifier 22*b* is used to drive a speaker 22 so that noise is suppressed. In FIG. 8, reference numeral 26*c* represents an FIR (Finite Inpulse Response) type compensating filter having a transfer function $\hat{E}$ provided for simulating a transfer function E of a sound field in which a speaker 22 and the microphone 21 are provided. Reference numeral 26*a* represents an FIR filter with its filter factor controlled by an LMS signal processing circuit 26*b*. The foregoing filters constitute the adaptive filter 26.

An exemplary conventional system is schematically shown in a block diagram in FIG. 9 exemplifies active noise-suppressive control having two degrees of freedom to which feedforward control is applied. A noise-suppressive control controller 271 of this exemplary system is provided with a feedback controller 28 and a feedforward controller 29 which are adaptive filters to perform noise-suppressive control by using adaptive FIR filters based on filtered-X-LMS signal processing for the feedback controller 28 and the feedforward controller 29. In FIG. 9, ($Z^{-1}$) represents a shift operator in a direction of delay. In FIG. 9, a control source corresponds to a sound source for counteracting noise, for example, a first speaker. A noise source corresponds to a sound source for producing noise, for example, a second speaker. An observer corresponds to a first microphone for detecting a difference between an output sound from the control source and an output sound from the noise source. A detector corresponds to a second microphone for detecting a reference signal. Reference numeral 37*a* represents a transfer function $Gr(Z^{-1})$ in a sound field between the noise source and the observer. Reference numeral 37*b* represents a transfer function $G(Z^{-1})$ in a sound field between the control source and the observer. Reference numeral 37*c* represents an FIR filter which has a transfer function obtained by simulating the transfer function $G(Z^{-1})$. The reference signal q(k) detected by the detector is supplied to the feedforward controller 29. A difference between an output of the feedforward controller 29 and an output of the feedback controller 28 is obtained by an adder 36*e*. An output of the adder 36*e* is used to control the control source. An error signal (y) as a difference between the noise from the noise source and an output from the control source is obtained by an adder 36*c*. A difference between the output of the adder 36*e* passed through the FIR filter 37*c* and the error signal (y) is obtained by an adder 36*d*, which is supplied to the feedback controller 28 to perform noise control for the sound field. In FIG. 9, an adder 36*a* is provided as an adder for combining periodical noise l(k) non-correlative to the reference signal q(k) and noise n(k) correlative to the reference signal q(k). An adder 36*b* is provided as an adder for combining the noise n(k) correlative to the reference signal q(k) and measured noise d(k) to obtain the reference signal q(k).

An exemplary conventional system is schematically shown in a block diagram in FIG. 10, in which a feedback controller 30 comprises, for example, an adaptive filter 31 controlled by LMS signal processing, an internal model 32 as a model of a plant 34, and an adder 33. An output of the adaptive filter 31 is supplied to the plant 34 having a transfer function P(s) and the internal model 32 having a transfer function $\hat{P}(s)$. The arrangement as described above, i.e., the arrangement, in which the plant 34 and the model (internal model) of the plant 32 are arranged in parallel, is called the internal model controller (IMC). In FIG. 10, an error signal (Y), which is a difference between an output of the plant 34 and noise (d), is detected by an adder 35. A difference x between an output signal from the adder 35 and an output signal from the internal model 32 is detected by an adder 33. The adaptive filter 31 is controlled on the basis of the output x detected by the adder 33 to perform noise-suppressive control so that the output signal of the adder 35 is controlled to be "0".

The adaptive filter 31 comprises the internal model 31*a*, an inverting unit 31*d* for inverting polarity of the output x, a signal processing unit 31*b* for performing arithmetic operation of adaptive algorithm based on the LMS method, and an FIR filter 31*c* having its filter factor updated in accordance with an output of the signal processing unit 31*b*.

SUMMARY OF THE INVENTION

In the conventional active noise-suppressive control, the adaptive filter is used not only for the feedforward controller but also for the feedback controller. Accordingly, the amount of arithmetic operation for the adaptive algorithm for controlling the adaptive filter is enormous as described in Japanese Laid-open Patent Publication No. 1-501344 (PCT) and Japanese Laid-open Patent Publication No. 8-30278. For this reason, the conventional active noise-suppressive control suffers an extremely large amount of digital operation processing required to perform the arithmetic operation of the adaptive algorithm, taking a long time for operation processing. If an operation processing unit having a low operation processing speed is used, a problem arises in that the noise-suppressive control cannot be performed at a high speed, resulting in inferior response in noise control.

If it is intended to shorten the operation processing time, a signal processing unit having a high operation speed is required, which results in a problem that an obtained active noise-suppressive control apparatus becomes expensive upon packaging of an active noise-suppressing unit.

A principle object of the present invention is to provide an active noise-suppressive control method and an apparatus which can be managed with less operation processing, making it possible to perform sufficient noise-suppressive control.

Another object of the present invention is to provide an active noise control method and an apparatus which can decrease load on a signal processing unit, making it possible to perform sufficient noise-suppressive control.

Still another object of the present invention is to provide an active noise control method and an apparatus in order to perform noise-suppressive control by previously estimating an amount of variation of a transfer function of a plant as additive perturbation.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

The active noise-suppressive method and the apparatus according to the present invention will be explained below with reference to embodiments.

Figure 1:
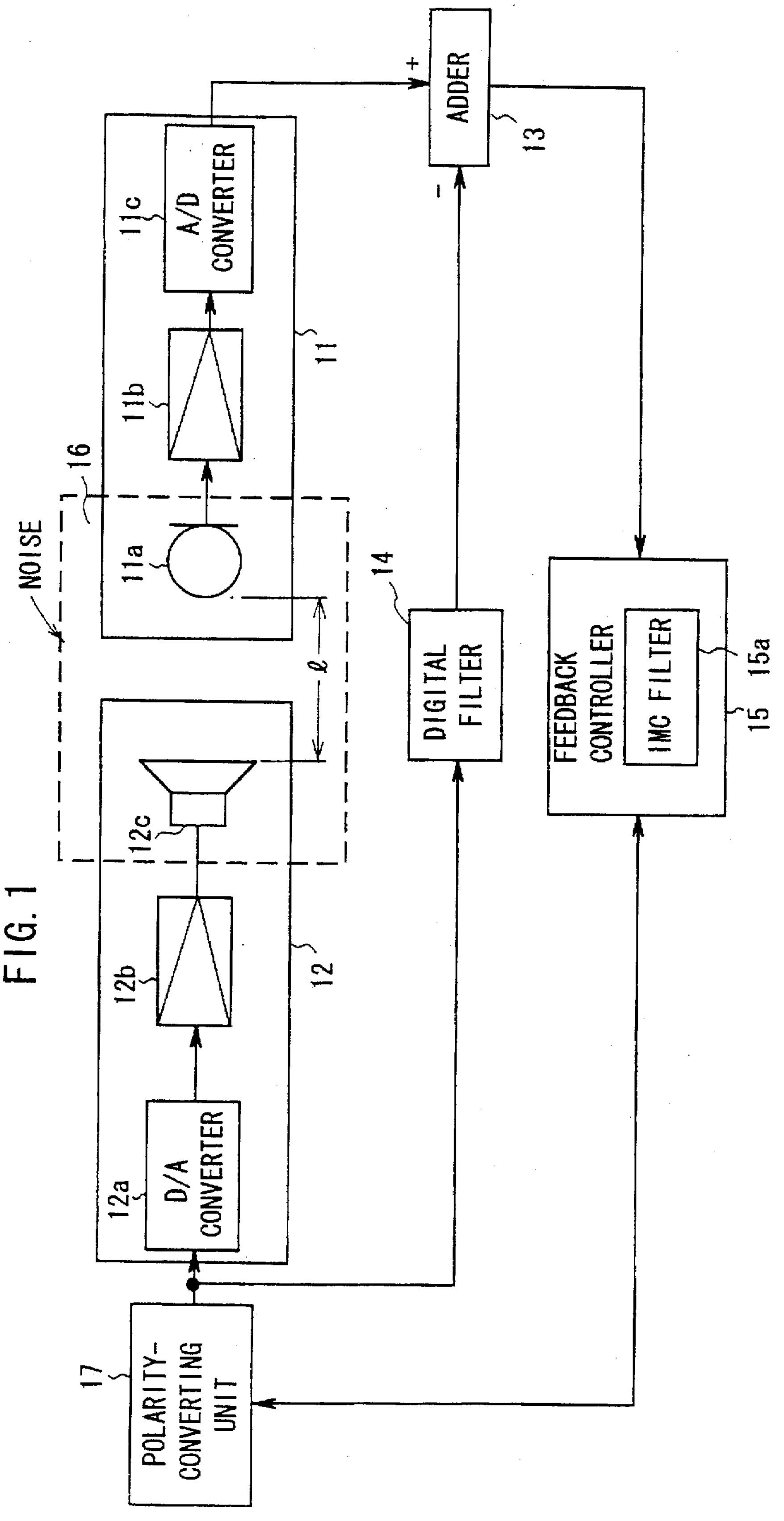
FIG. 1 shows a block diagram illustrating an arrangement of an active noise-suppressive control apparatus according to an embodiment of the present invention.
Figure 2:
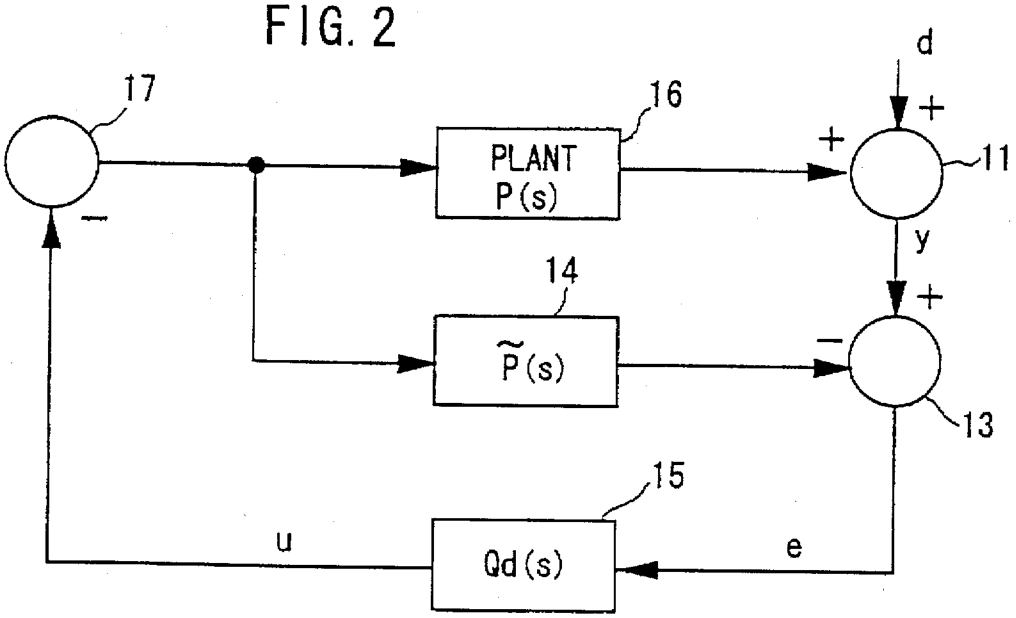
FIG. 2 shows a block diagram illustrating the active noise-suppressive control apparatus according to the embodiment of the present invention.

FIGS. 1 and 2 show block diagrams illustrating an arrangement of an active noise-suppressive control apparatus according to an embodiment of the present invention respectively.

In FIG. 1, a sound source unit 12 is provided in a sound field 16, for canceling noise. An error signal sensor 11A is provided at a silencing point in the sound field 16, for sending an error signal based on a difference between a noise coming from the outside of the sound field 16 and a reproduced sound from the sound source unit 12. The error signal sensor 11 comprises a microphone 11*b*, an amplifier 11*b* for amplifying the error signal outputted from the microphone 11*a*, and an AD converter 11*c* for converting an output signal of the amplifier 11*b* into a digital signal. The sound source unit 12 comprises a D/A converter 12*a* for converting a speaker-driving signal into an analog signal, an amplifier 12*b* for amplifying the analog signal converted by the D/A converter 12*a*, and a speaker 12*c* driven in accordance with an output of the amplifier 12*b*. The distance between the speaker 12*c* and the microphone 11*a* is 1, and the sound field 16 is regarded as a plant.

A digital filter 14 comprising, for example, an FIR filter is provided as an internal model that is a model for the plant, having a transfer function established as a fixed transfer function $\tilde{P}(s)$ which is approximated to a transfer function $P(s)$ of the plant. An output signal from the digital filter 14 is subtracted from an output signal of the A/D converter 11*c* by an adder 13. An output signal from the adder 13 is supplied to a feedback controller 15 comprising an internal controller (IMC) filter 15*a*. An output signal of the feedback controller 15 is supplied to a polarity-inverting unit 17 to invert its polarity. An obtained signal is supplied to the digital filter 14 and the D/A converter 12*a* included in the sound source unit 12. Thus the noise is canceled by using a reproduced sound of the speaker 12*c*.

The digital filter 14 has its transfer function which is the fixed transfer function. The fixed transfer function is set to be approximate to the transfer function of the plant. Moreover, the driving signal for the sound source unit 12 is supplied as the input signal. Accordingly, the amount of variation of the transfer function of the plant is substantially detected. The feedback controller 15 compensates variation of the transfer function of the plant and variation of the noise in the sound field 16.

In FIG. 2, P(s) indicates the transfer function of the plant. $\tilde{P}(s)$ indicates the transfer function of the digital filter 14. Qd(s) indicates a transfer function of the feedback controller 15.

Now assuming that the sound field 16 including the speaker 12*c* and the microphone 11*a* is a free sound field, the transfer function P(s) of the plant is determined by Laplace-transforming a wave equation of a spherical wave.

The transfer function P(s) is represented by the following expression (1).

$$P(s)=\frac{A}{l}e^{-\tau s} \quad (1)$$

In the expression (1), A is a constant, and l is the distance from the speaker 12*c* to the microphone 11*a* as described above. Assuming that c is the speed of sound, τ (=l/c) represents a dead time. Thus the plant, which is an object of the feedback active noise-suppressive control, is a dead time system. The dead time system is an infinite dimension system, which is generally difficult to be controlled.

In the active noise-suppressive control according to the embodiment of the present invention, the dead time is subjected to Pade approximants to obtain $\tilde{P}(s)$ represented by the following expression (2) which is used as the transfer function of the digital filter 14 that serves as the internal model.

$$\left.\begin{aligned}\tilde{P}(s) &= \frac{1}{l}\cdot\frac{-as+1}{as+1}\\ a &= \frac{\tau}{2}\end{aligned}\right] \quad (2)$$

The control system, in which the transfer function of the plant and the transfer function of the digital filter 14 as its model are arranged in parallel to input an identical signal into them so that a difference between their outputs is subjected to feedback as an error, is called the internal model controller (IMC) which is known to be excellent in robust performance.

The IMC system is used for the feedback system in the active noise-suppressive control according to the embodiment of the present invention. In the case of the IMC system, it is known that the feedback system is stable provided that the feedback controller 15 is designed to be stable when the transfer function $P(s)=\tilde{P}(s)$.

In FIG. 1, a transfer function S(s) concerning a region from the noise source to an end of the microphone 11*a* for error signal generation is called the sensitivity function which is represented by the following expressions (3) and (4).

$$y(s)=S(s)\cdot d(s) \quad (3)$$

wherein d(s) is obtained by Laplace-transforming the noise.

$$S(s)=\frac{1-\tilde{P}(s)Qd(s)}{1+Qd(s)\{P(s)-\tilde{P}(s)\}} \quad (4)$$

In the feedback active noise-suppressive control, the noise is reduced if the sensitivity function S(s) can be made smaller than 1 in a control-objective frequency zone. Namely, the control objective of noise reduction is nothing but the decrease in sensitivity function S(s) to be smaller than 1.

Now a nominal case will be explained in which the transfer function $\tilde{P}(s)$ of the digital filter 14 as the internal model is equal to the transfer function P(s) of the plant.

In the nominal case, the transfer function Qd(s) is referred to as $\tilde{Q}d(s)$.

In this case, the expressions (3) and (4) described above are represented by the following expressions (5) and (6).

$$y(s)=\tilde{S}(s)\cdot d(s) \quad (5)$$

$$\tilde{S}(s)=1-\tilde{P}(s)\tilde{Q}d(s) \quad (6)$$

Therefore, if the plant is a minimum phase system, the influence of external disturbance can be made zero by making selection in accordance with the following expression (7). However, the plant is a non-minimum phase system in the active noise-suppressive control according to the embodiment of the present invention. Accordingly, the transfer function $\tilde{P}(s)$ is subjected to inner-outer decomposition as shown in the following expression (8).

$$\tilde{Q}d(s)=\frac{1}{\tilde{P}(s)} \quad (7)$$

$$\tilde{P}(s)=P_M(s)P_A(s) \quad (8)$$

In the expression (8), $P_M(s)$ is a minimum phase function, and $P_A(s)$ is an entire region-passing function. They are given respectively as shown in the following expression (9). It is assumed that A=1.

$$P_M(s)=\frac{1}{l}\ ,\ P_A(s)=\frac{-as+1}{as+1} \quad (9)$$

If step-shaped external disturbance d(s)=1/s is assumed in order to facilitate the analysis from a viewpoint of inclusion of wide band frequency components, the minimum error norm for the step-shaped external disturbance is obtained in accordance with the following expression (10).

$$\min_{\tilde{Q}d}\|y(s)\|_2^2=\frac{2Re(1/a)}{|1/a|^2}=2a=\tau=\frac{l}{c} \quad (10)$$

The minimum error norm shown in the expression (10) comes to a minimum value when a relationship shown in the following expression (11) is established.

$$\tilde{Q}d(s)=\frac{1}{P_M(s)} \quad (11)$$

The minimum error norm shown in the expression (10) indicates the fact that achievable $H_2$ norm increases if unstable zero point is present near to the origin. Therefore, in the active noise-suppressive control according to the embodiment of the present invention, it is indicated that the unstable zero point approaches the origin as the distance 1 from the speaker 12*c* to the microphone 11*a* becomes long, resulting in difficult noise-suppressive control.

Next, the robust stability of the active noise-suppressive control according to the embodiment of the present invention will be explained.

It is assumed that the existing range of the plant (set of uncertainty) may be described by additive perturbation shown in the following expression (12).

$$\Pi a=\{P:|P(j\omega)-\tilde{P}(j\omega)|\leq Wa(j\omega)\} \tag{12}$$

Wa(jω) is a frequency weight function for covering a systematic error of the plant. In this case, it is known that the condition for robust stability is represented by the following expression (13).

$$\|\tilde{T}a(s)Wa(s)\|_\infty<1 \tag{13}$$

In the expression (13), $\tilde{T}a(s)$ is a quasi-complementary sensitivity function defined as the following expression (14).

$$\tilde{T}a(s)=Qd(s) \tag{14}$$

In the IMC system, the IMC filter 15*a* comprising a low-pass filter is used in the feedback controller 15. When the transfer function of the IMC filter 15*a* is represented by F(s), the transfer function Qd(s) of the feedback controller 15 is represented by the following expression (15).

$$Qd(s)=\tilde{Q}d(s)F(s) \tag{15}$$

Therefore, the robust stability condition can be represented by the following expression (16) in the range of all angular velocities ω(=2πf) by using the expressions (14) and (15).

$$|\tilde{Q}d(j\omega)F(j\omega)Wa(j\omega)|<1,\ \forall\omega \tag{16}$$

In this case, the step-shaped external disturbance is assumed as described above. Accordingly, a transfer function shown in the following expression (17) is selected as the transfer function F(s) of the IMC filter 15*a* by using λ as a variable parameter of the IMC filter 15*a*. Taking notice of the fact that $\tilde{Q}d(s)$ is represented by the following expression (18), the expression (16), which indicates the condition of robust stability, comes to the following expression (19).

$$F(s)=\frac{1}{\lambda s+1} \tag{17}$$

$$\tilde{Q}d(s)=P_M^{-1}(s)=l \tag{18}$$

$$|lF(j\omega)Wa(j\omega)|<1,\ \forall\omega \tag{19}$$

Now the variable parameter λ of the IMC filter 15*a* is adjusted so that the condition of robust stability is satisfied.

The transfer function Qd(s) of the feedback controller 15 can be determined as the following expression (20) by using the transfer function F(s) of the IMC filter 15*a* shown in the expression (17).

$$Qd(s)=l\cdot F(s) \tag{20}$$

The output u of the feedback controller 15 is obtained as follows by using the transfer function Qd(s) of the feedback controller 15 thus determined provided that the input signal of the feedback controller 15 is e.

$$u=Qd(s)e \tag{21}$$

Figure 3:
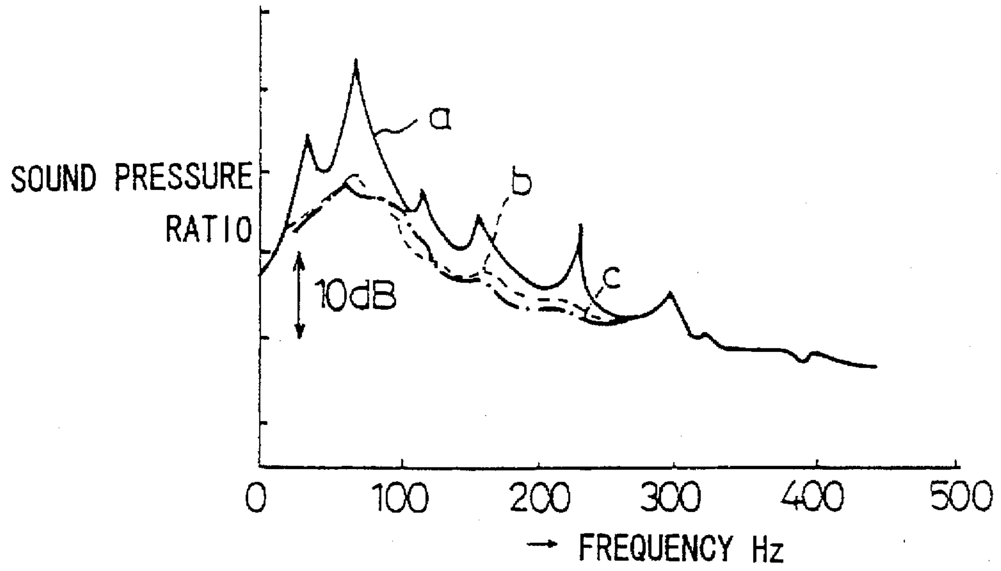
FIG. 3 shows a characteristic for explaining the noise-suppressive effect obtained by the active noise-suppressive control apparatus according to the embodiment of the present invention.

The system of the feedback controller 15, which resides in the determination in accordance with the expressions (20) and (21), is simple. The noise-suppressive effect obtained by using the feedback controller 15 having such a simple system is shown by a broken line b in FIG. 3, which is favorably comparable with the noise-suppressive effect obtained in accordance with the LMS method shown by a chain line c. A continuous line a in FIG. 3 indicates noise brought about when no noise-suppressive control is performed.

Now explanation will be made for the amount of arithmetic operation in the case of the adaptive control based on the use of the conventional LMS method, and the amount of arithmetic operation in the case of the active noise-suppressive control according to the embodiment of the present invention.

Figure 10:
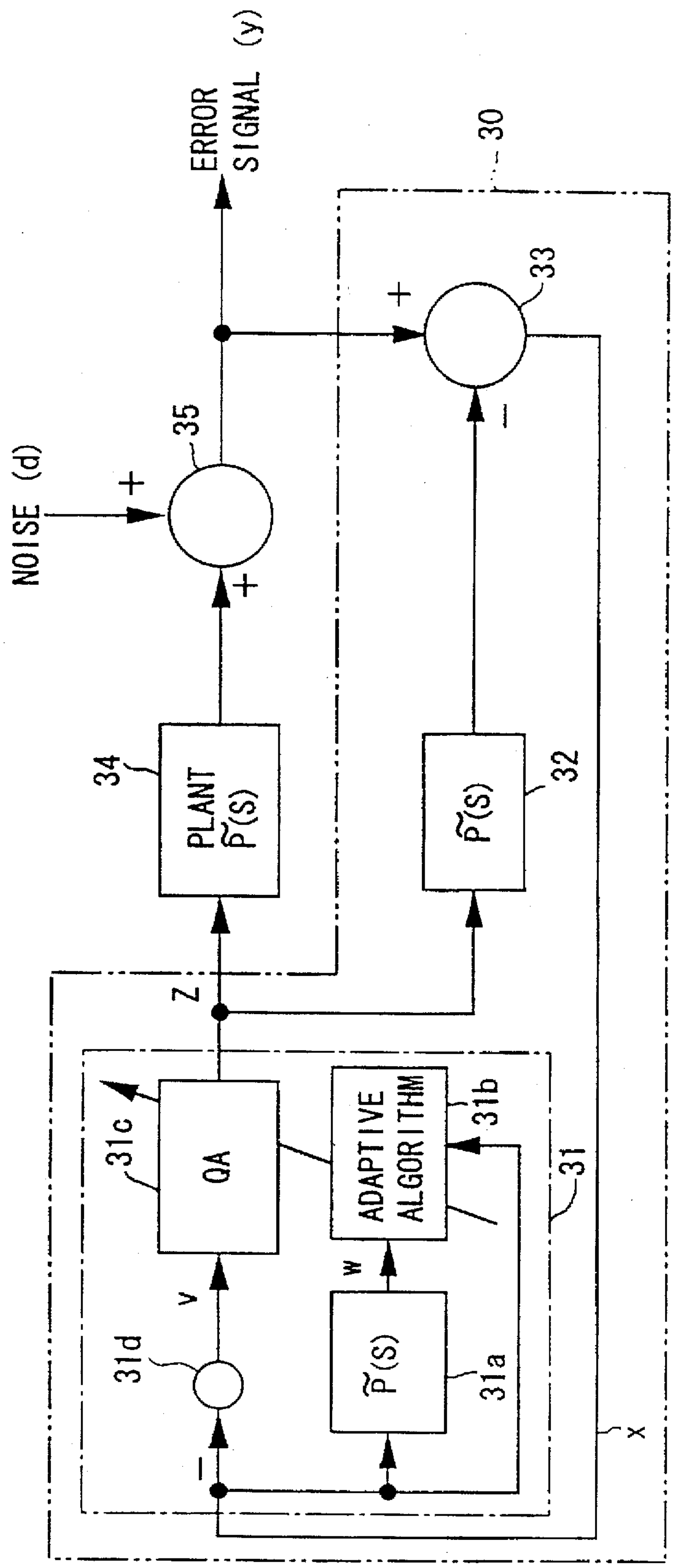
FIG. 10 PRIOR ART
FIG. 10 shows a block diagram illustrating an arrangement of still another conventional active noise-suppressive control apparatus.

As for the adaptive filter 31 shown in FIG. 10, arithmetic operations shown in the following expressions (22) to (24) are required provided that the input signal of the internal model 31*a* is x, the input of the signal processing unit 31*b* is w, the input signal of the FIR filter 31*c* is v, and the output signal of the FIR filter 31*c* is z.

$$z=Q_A v \tag{22}$$

$$W=\tilde{P}(s)x \tag{22}$$

$$Q_A(\text{new})=Q_A(\text{old})+\mu wx \tag{24}$$

In the foregoing, $Q_A$ represents the transfer function of the FIR filter 31*c*, and $\tilde{P}(s)$ represents the transfer function of the internal model 31*a*. μ is a step parameter calculated on the basis of the LMS method. On the contrary, the active noise-suppressive control according to the embodiment of the present invention only requires the expression (21). Operations for the expressions (23) and (24) are unnecessary. Thus the amount of arithmetic operation is greatly decreased.

For example, when the active noise-suppressive control according to the embodiment of the present invention is applied to noise-suppressive control in a vehicle's cabin, the transfer function P(s) of the plant changes on the basis of external disturbance factors and internal disturbance factors. The external disturbance factors include, for example, increase or decrease in number of passengers, and states of opening or closing windows. The internal disturbance factors are caused by secular change in the microphone 11*a* and the speaker 12*c*, and the error between the transfer function P(s) of the plant and the transfer function $\tilde{P}(s)$ of the digital filter 14 as the internal model. The amount of variation of the transfer function P(s) is approximated and set by previously estimating it as additive perturbation with respect to the frequency. In this case, the additive perturbation shown in the expression (12) corresponds to the estimation of the amount of variation of the transfer function of the plant. The estimation is previously performed before packaging.

Further, the variable parameter λ of the IMC filter 15*a* is adjusted so that the condition of robust stability shown in the expression (16) is satisfied.

Specifically, the distance l from the speaker 12*c* to the microphone 11*a* is physically definite. The frequency weight function for covering the amount of variation is a amount of variation of the approximated and set transfer function P(s), which is previously approximated and set. Therefore, the transfer function F(s) of the IMC filter 15*a* is selected by previously adjusting the variable parameter λ so that |l·F(s)·Wa(s)|<1 is given, i.e., the condition of robust stability is satisfied. The transfer function Qd(s) of the feedback controller 15 is determined in accordance with the expression

(20) by using the selected transfer function F(s). Thus the system of the feedback controller 15 is unexpectedly simple.

Therefore, it is unnecessary to always perform arithmetic operation in order to follow variation of the transfer function of the plant in real time, which would be otherwise performed in the conventional adaptive control. The amount of arithmetic operation is unexpectedly small as described above. Moreover, the system of the feedback controller 15 is simple.

The variable parameter λ is selected so that |l·F(s)·Wa(s)| approaches "1" as near as possible. This is because of the following reason. Namely, a large noise-suppressive effect is obtained by allowing |l·F(s)·Wa(s)| to approach "1" as near as possible.

Figure 4:
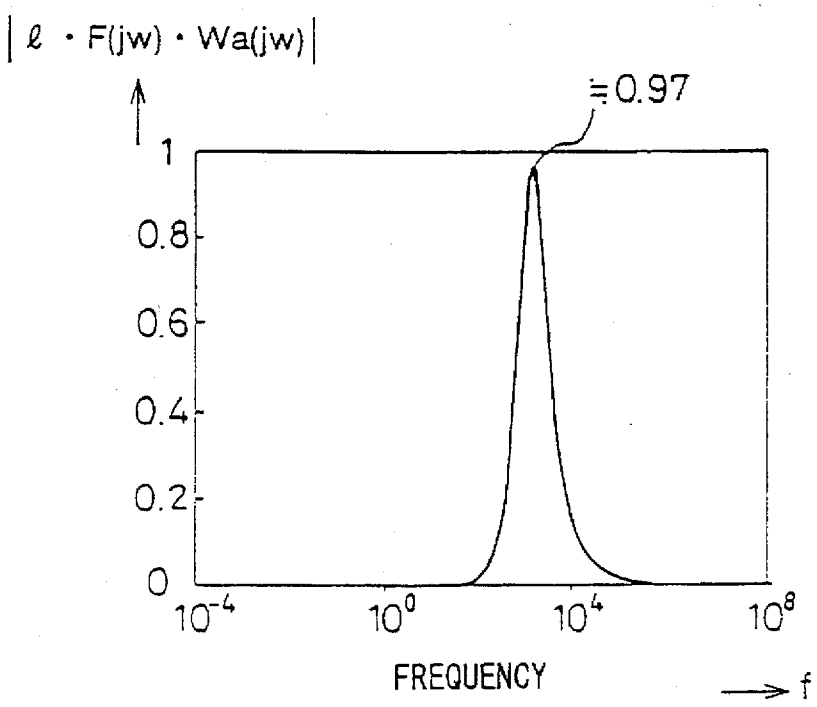
FIG. 4 shows a characteristic for explaining selection of a variable parameter of an IMC filter used in the active noise-suppressive control apparatus according to the embodiment of the present invention.

Specifically, selection was made to give F(s)=1/(0.0002s+1) when the distance l from the speaker 12*c* to the microphone 11*a* was 0.2 m. In this case, the condition of robust stability |l·F(jω)·Wa(jω)| was provided as shown in FIG. 4, and a maximum value of 0.97 was obtained. It is preferred that the variable parameter λ is selected so that the condition of robust stability |l·F(jω)·Wa(jω)| is less than 1 and not less than 0.9.

Next, explanation will be made for estimation of the amount of variation of the transfer function P(s) of the plant 16.

Namely, the frequency weight function Wa(s) is set so as to cover the difference between the transfer function P(s) of the plant shown in the expression (1) and the transfer function $\tilde{P}(s)$ of the digital filter 14 as the internal model approximated in the expression (2).

Figure 5A:
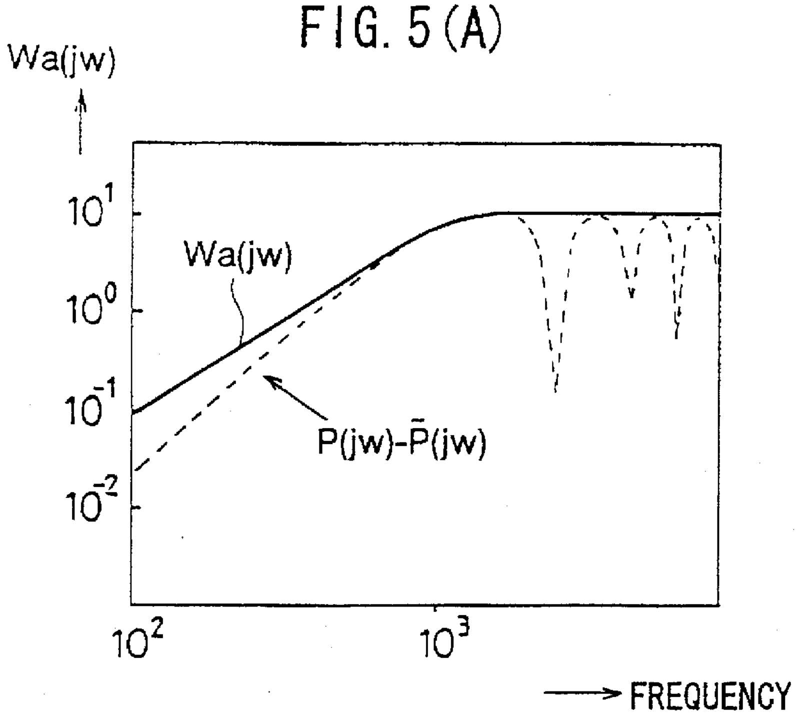
FIG. 5(A) shows an explanatory drawing for explaining setting of a frequency weight function used in the active noise-suppressive control according to the embodiment of the present invention.

When the distance l from the speaker 12*c* to the microphone 11*a* is 0.2 m, the frequency weight function Wa(jω) is set as shown by a continuous line shown in FIG. 5(A). In FIG. 5(A), a broken line indicates additive perturbation (P(jω)−$\tilde{P}$(jω)). The value of the frequency weight function Wa(jω) is determined in a manner of trial and error. However, the value of the frequency weight function Wa(jω) is set such that it is not less than the additive perturbation, and it asymptotically approaches the additive perturbation. In the embodiment shown in FIG. 5(A), the frequency weight function Wa(s) is set as shown in the following expression (25).

$$Wa(s)=\frac{700\tau s^2}{l^2\left[s-\frac{-850+j1100}{l}\right]}\times\frac{1}{\left[s+\frac{-850+j1100}{l}\right]} \quad (25)$$

Figure 5B:
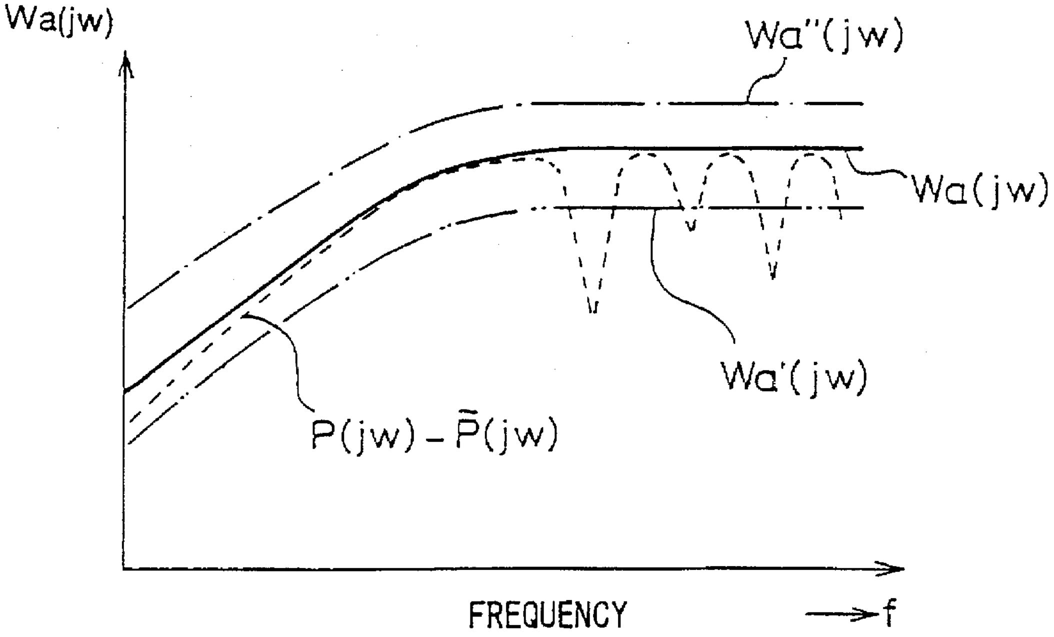
FIG. 5(B) shows another explanatory drawing for explaining setting of a frequency weight function used in the active noise-suppressive control according to the embodiment of the present invention.

As shown in FIG. 5(B), if the frequency weight function Wa(s) is set as a frequency weight function Wa(jω)" represented by a chain line higher than an envelope of the additive perturbation, the noise is not sufficiently suppressed. If the frequency weight function Wa(s) is set as a frequency weight function Wa(jω)' represented by a two-dot chain line lower than the weight function Wa(s) which asymptotically approaches the additive perturbation, the system becomes unstable with the occurrence of howling or the like.

Therefore, it is most preferable that the frequency weight function Wa(jω) is set such that it is not less than the additive perturbation, and it asymptotically approaches the additive perturbation.

Now explanation will be made for another method for estimating the amount of variation of the transfer function P(s) of the plant with reference to FIG. 6.

Figure 6:
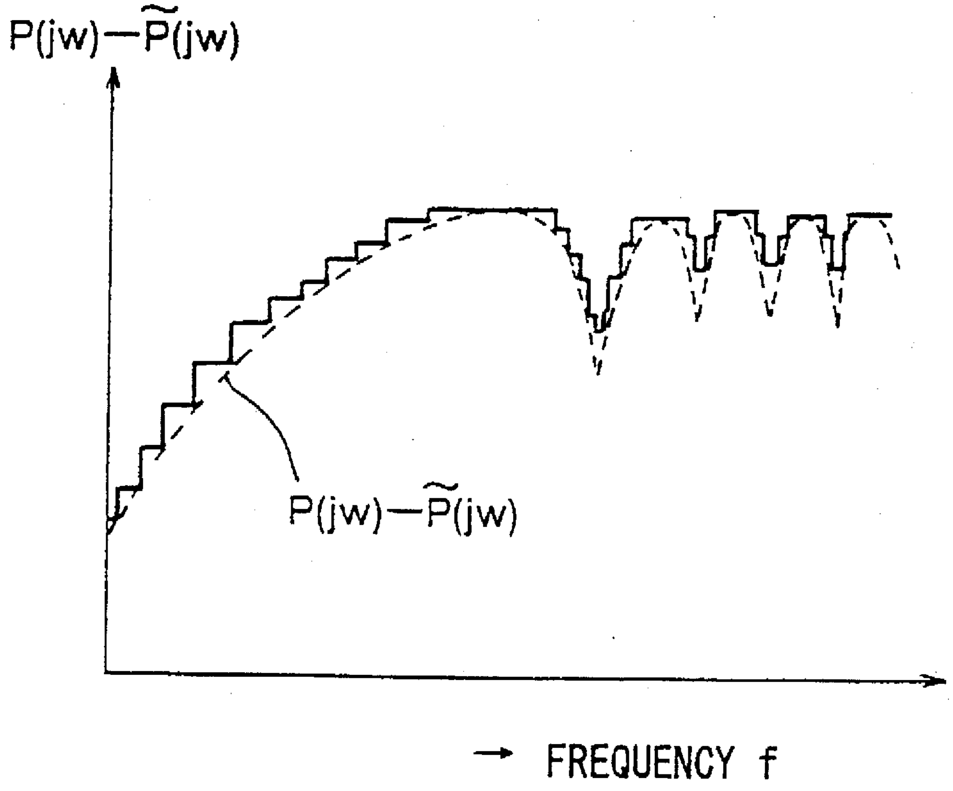
FIG. 6 shows an explanatory drawing for approximating and selecting an amount of variation of a transfer function of a plant used in the active noise-suppressive control apparatus according to the embodiment of the present invention.
Figure 7A:
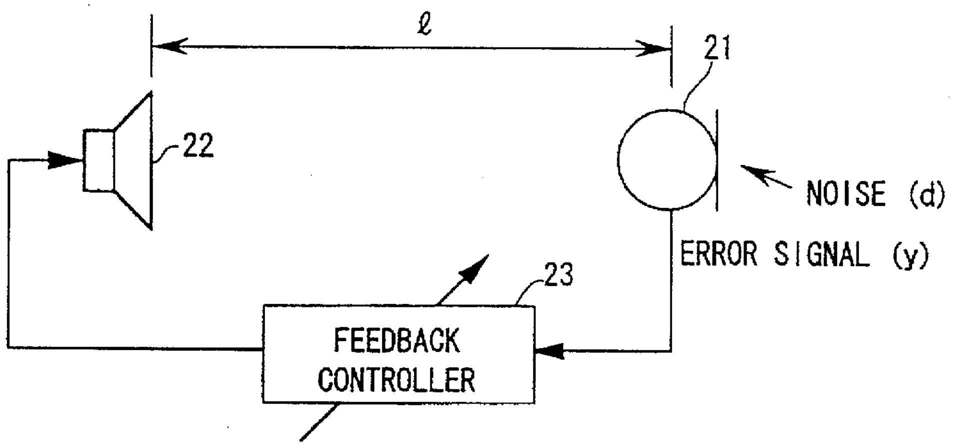
FIG. 7(A) PRIOR ART
FIG. 7(A) shows a block diagram illustrating a conventional active noise-suppressive control apparatus.
Figure 7B:
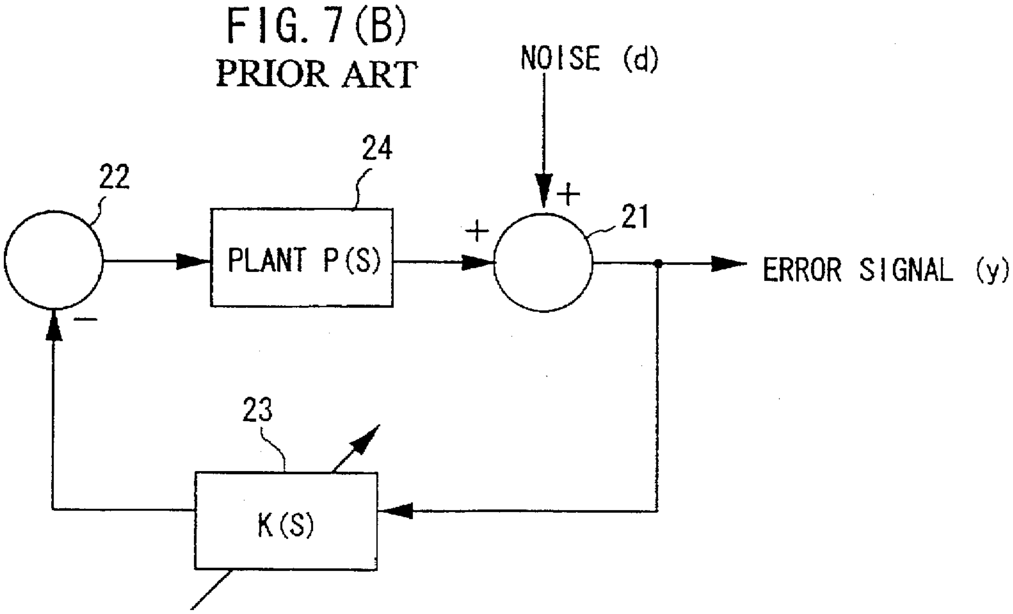
FIG. 7(B) PRIOR ART
FIG. 7(B) shows a block diagram illustrating the conventional active noise-suppressive control apparatus.
Figure 8:
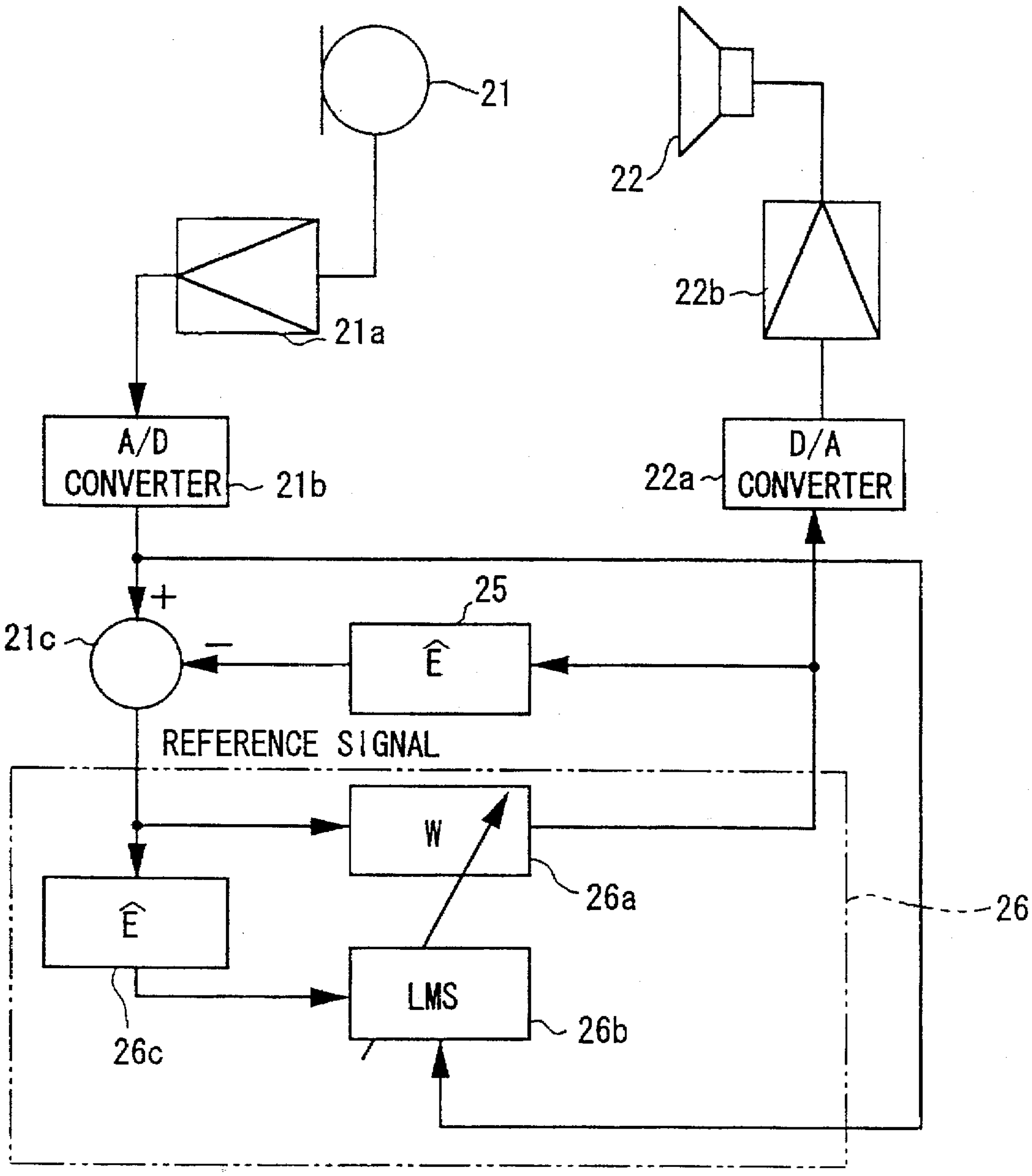
FIG. 8 PRIOR ART
FIG. 8 shows a block diagram illustrating an arrangement of another conventional active noise-suppressive control apparatus.
Figure 9:
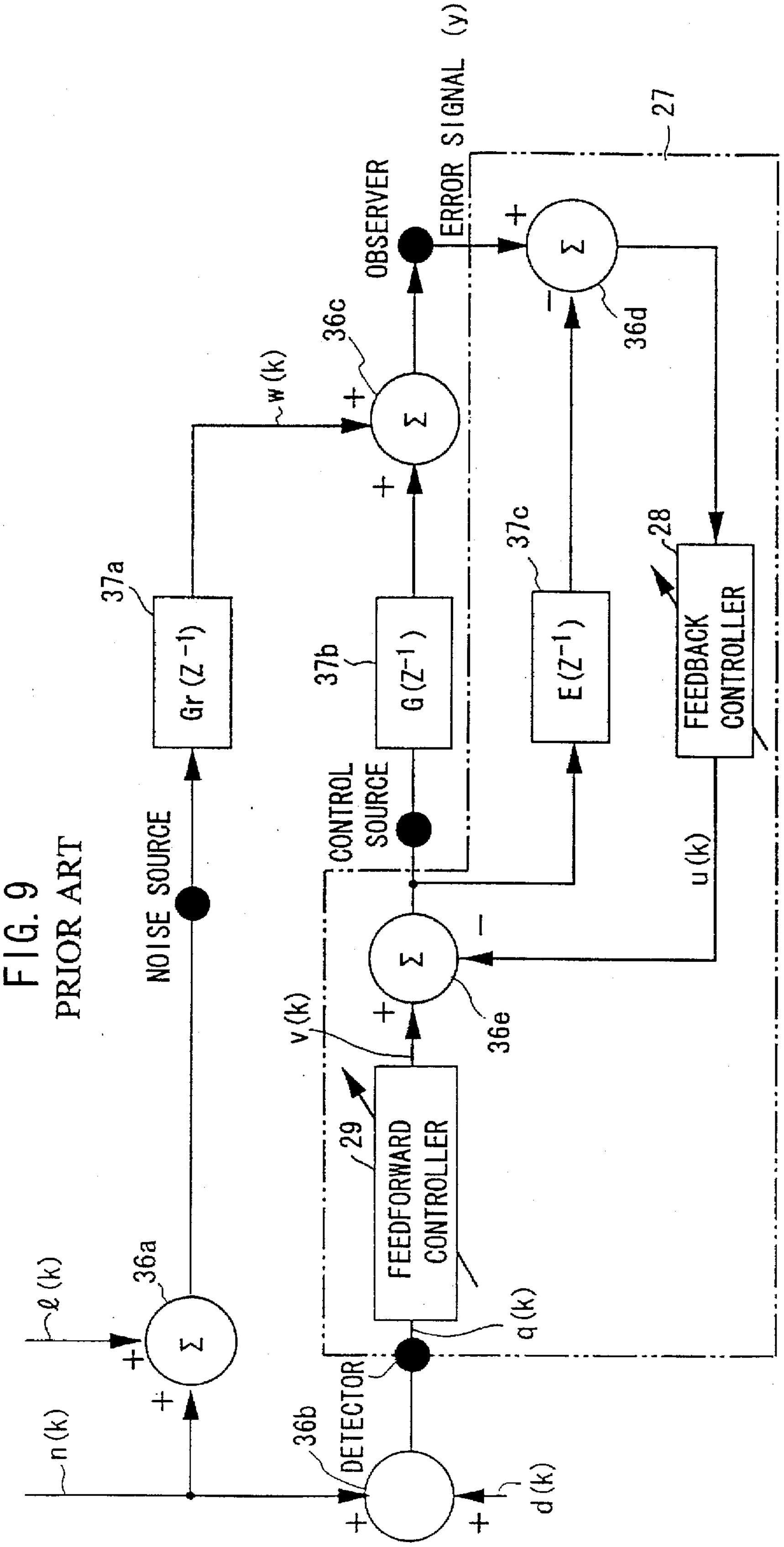
FIG. 9 PRIOR ART
FIG. 9 shows a block diagram illustrating an arrangement of still another conventional active noise-suppressive control apparatus.

In FIG. 6, a broken line indicates additive perturbation (P(jω)−$\tilde{P}$(jω)) with respect to the frequency. In another method for estimating the amount of variation, the amount of variation of the transfer function P(s) is estimated in accordance with an amount of step-shaped variation which is closely near to the additive perturbation shown by the broken line in FIG. 6.

In the case of estimation as described above, the amount of variation of the transfer function P(s) is previously set with respect to the frequency. Accordingly, the degree of freedom is increased upon approximation of the amount of variation depending on a form of change of the amount of variation. Thus it is possible to select the variable parameter of the IMC filter 15*a* highly accurately.

As explained above, according to the active noise-suppressive control of the present invention, the amount of variation of the transfer function is previously approximated and set with respect to the frequency. Accordingly, it is sufficient for the system to set the variable parameter of the IMC filter as a constant so that the product of the approximated and set amount of variation of the transfer function, the distance from the sound source to the error-detecting sensor, and the transfer function of the IMC filter is less than 1. Accordingly, an enormous amount of arithmetic operation is unnecessary, which would be otherwise required for the conventional adaptive control that allows the system to follow the variation of the transfer function. Thus an effect is obtained in that the amount of arithmetic operation is unexpectedly small.

According to the active noise-suppressive control of the present invention, the system for the noise-suppressive control can be constructed by using the simple feedback controller. An effect is also obtained in that the operation processing time required for noise suppression is decreased, and the response performance is improved. Further, the system can be constructed inexpensively upon packaging. Moreover, according to the active noise-suppressive control of the present invention, an effect is obtained in that a signal processing unit having a slow operation processing speed is sufficiently used if the processing time is allowed to be identical with that of the conventional adaptive control.

According to the active noise-suppressive control of the present invention, when the approximated and set amount of variation of the transfer function is represented by the frequency weight function, the product of the amount of variation of the transfer function, the distance from the sound source unit to the error-detecting sensor, and the transfer function of the IMC filter is obtained as the function of the frequency. Accordingly, an effect is obtained in that the variable parameter of the IMC filter is easily selected.

The amount of variation of the transfer function is previously set with respect to the frequency in the active noise-suppressive control according to the present invention. Therefore, the degree of freedom upon the approximation of the amount of variation increases depending on the form of change of the amount of variation. Thus an effect is obtained in that the variable parameter of the IMC filter can be accurately selected.

If the amount of variation of the transfer function is set to be the amount of variation not less than the estimated amount of variation or the actually measured amount of variation affected by the internal and external disturbance factors of the transfer function, the noise-suppressive effect is lowered, and the remaining noise increases. On the contrary, if the amount of variation of the transfer function is set to be the amount of variation less than the estimated amount of variation or the actually measured amount of variation affected by the internal and external disturbance factors of the transfer function, the noise suppression is unstable, and howling occurs. However, in the active noise-suppressive control according to the present invention, the amount of variation of the transfer function is the amount of variation which is not less than the estimated amount of variation or the actually measured amount of variation affected by the internal and external disturbance factors of the transfer function and which asymptotically approaches the estimated amount of variation or the actually measured amount of variation. Thus the noise-suppressive effect is maximized, and the noise-suppressive effect is stably obtained.

What is claimed is:

1. An active noise-suppressive control method comprising the steps of:

producing an error signal by monitoring a difference between noise coming from the outside of a sound field into the inside of said sound field and vibration for canceling said noise, and producing said error signal on the basis of said difference;

detecting a difference signal between said error signal and an output signal from a model having a fixed transfer function which is approximately equal to a transfer function of said sound field, a driving signal for producing said vibration for canceling said noise being supplied to said model so that variation of said transfer function of said sound field is detected;

IMC-filtering said difference signal to produce a noise cancel signal;

inverting polarity of said noise cancel signal to supply a polarity-inverted noise cancel signal as an input signal to said model;

converting said polarity-inverted noise cancel signal into said vibration for canceling said noise to supply, to said sound field, said cancel vibration for counteracting said noise coming into the inside of said sound field; and selecting a variable parameter of an IMC filter for said IMC filtering by previously approximating and setting an amount of variation of said transfer function of said sound field affected by internal and external disturbance factors, as additive perturbation over a predetermined range of frequency so that an absolute value of a product of said approximated and set amount of variation, a distance from a position in said sound field for supplying said cancel vibration to a position for monitoring said difference between said noise coming from the outside of said sound field into the inside of said sound field and said vibration for canceling said noise, and a transfer function of said IMC filter is less than 1.

2. The active noise-suppressive control method according to claim 1, wherein said step of detecting uses a digital filter as said model.

3. The active noise-suppressive control method according to claim 1, wherein said step of detecting uses an FIR digital filter as said model.

4. The active noise-suppressive control method according to claim 1, wherein said step of selecting uses a frequency weight function as said previously approximated and set amount of variation of said transfer function of said sound field.

5. The active noise-suppressive control method according to claim 1, wherein said step of selecting uses an amount of variation previously set with respect to said frequency, as said previously approximated and set amount of variation of said transfer function of said sound field.

6. The active noise-suppressive control method according to claim 1, wherein said step of selecting uses an amount of variation which is not less than an estimated amount of variation or an actually measured amount of variation of said transfer function affected by said internal and external factors and which asymptotically approaches said estimated amount of variation or said actually measured amount of variation, as said amount of variation of said transfer function of said sound field affected by said internal and external disturbance factors.

7. The active noise-suppressive control method according to claim 1, wherein said step of selecting uses a value which is not less than 0.9 and less than 1, as said absolute value of said product.

8. An active noise-suppressive control apparatus comprising:

a sound source unit provided in a sound field;

an error-detecting unit, provided in said sound field, for detecting a difference between noise coming from the outside of said sound field into the inside of said sound field and vibration outputted from said sound source unit;

a model having a fixed transfer function approximated to a transfer function of said sound field, to which a signal for driving said sound source unit is supplied;

an operation means for calculating a difference between an output signal outputted from said error-detecting means and an output signal outputted from said model; and an IMC filter for using an output signal outputted from said operation means as an input signal, and using a signal obtained by inverting polarity of said output signal as said driving signal for said sound source unit and as an input signal inputted into said model; wherein an amount of variation of said transfer function of said sound field affected by internal and external disturbance factors is previously approximated and set as additive perturbation over a predetermined range of frequency, a variable parameter of said IMC filter is selected so that an absolute value of a product of a value of said approximated and set amount of variation, a distance from said sound source unit to said error-detecting unit, and a transfer function of said IMC filter is less than 1, said sound source unit is driven by a signal based on an output signal of said IMC filter in which said variable parameter is set, and said noise coming into the inside of said sound field is counteracted by using output vibration of said sound source unit.

9. The active noise-suppressive control apparatus according to claim 8, wherein said model is a digital filter.

10. The active noise-suppressive control apparatus according to claim 8, wherein said model is an FIR digital filter.

11. The active noise-suppressive control apparatus according to claim 8, wherein said IMC filter is a low-pass filter.

12. The active noise-suppressive control apparatus according to claim 8, wherein said previously approximated and set amount of variation of said transfer function of said sound field is a frequency weight function.

13. The active noise-suppressive control apparatus according to claim 8, wherein said previously approximated and set amount of variation of said transfer function of said sound field is an amount of variation previously set with respect to said frequency.

14. The active noise-suppressive control apparatus according to claim 8, wherein said amount of variation of said transfer function of said sound field affected by said internal and external disturbance factors is an amount of variation which is not less than an estimated amount of variation or an actually measured amount of variation affected by said internal and external factors of said transfer function and which asymptotically approaches said estimated amount of variation or said actually measured amount of variation.

* * * * *